United States Patent
Sugimoto et al.

(10) Patent No.: US 9,167,815 B2
(45) Date of Patent: Oct. 27, 2015

(54) AGRICULTURAL OR HORTICULTURAL FUNGICIDE COMPOSITION AND METHOD FOR CONTROLLING PLANT PATHOGEN

(75) Inventors: Koji Sugimoto, Shiga (JP); Takanori Suzuki, Shiga (JP); Koudai Yamamoto, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 140 days.

(21) Appl. No.: 14/119,230

(22) PCT Filed: May 25, 2012

(86) PCT No.: PCT/JP2012/064253
§ 371 (c)(1),
(2), (4) Date: Nov. 21, 2013

(87) PCT Pub. No.: WO2012/161354
PCT Pub. Date: Nov. 29, 2012

(65) Prior Publication Data
US 2014/0187567 A1    Jul. 3, 2014

(30) Foreign Application Priority Data

May 25, 2011 (JP) ................................. 2011-117097

(51) Int. Cl.
| | | |
|---|---|---|
| A01N 43/40 | (2006.01) | |
| A01N 43/54 | (2006.01) | |
| A01N 37/50 | (2006.01) | |
| A01N 37/46 | (2006.01) | |
| A01N 43/56 | (2006.01) | |

(52) U.S. Cl.
CPC ............... *A01N 43/40* (2013.01); *A01N 37/46* (2013.01); *A01N 37/50* (2013.01); *A01N 43/54* (2013.01); *A01N 43/56* (2013.01)

(58) Field of Classification Search
CPC ........ A01N 43/40; A01N 43/54; A01N 37/50
USPC ......................................... 514/269, 352, 345
See application file for complete search history.

(56) References Cited

U.S. PATENT DOCUMENTS

| | | | |
|---|---|---|---|
| 4,331,670 | A | 5/1982 | Nishiyama et al. |
| 5,145,856 | A | 9/1992 | Clough et al. |
| 5,264,440 | A | 11/1993 | Clough et al. |
| 5,395,837 | A | 3/1995 | Clough et al. |
| 5,468,747 | A | 11/1995 | Clough et al. |

FOREIGN PATENT DOCUMENTS

| | | |
|---|---|---|
| CN | 101611711 A | 12/2009 |
| CN | 101755798 A | 6/2010 |
| CN | 101984817 A | 3/2011 |
| DE | 102004049761 A1 | 4/2006 |
| EP | 1 358 801 A1 | 11/2003 |
| JP | 5692272 A | 7/1981 |
| JP | 672140 B2 | 9/1994 |
| WO | 9603044 A1 | 2/1996 |
| WO | 9740687 A1 | 11/1997 |
| WO | 9825465 A1 | 6/1998 |
| WO | 9854965 A1 | 12/1998 |
| WO | 0219821 A1 | 3/2002 |
| WO | 03/092384 A1 | 11/2003 |
| WO | 2005094583 A1 | 10/2005 |
| WO | 2006/037632 A1 | 4/2006 |
| WO | 2006069699 A1 | 7/2006 |

OTHER PUBLICATIONS

International Search Report, PCT/ISA/210, dated Jan. 18, 2013, issued by the International Searching Authority in counterpart International Application No. PCT/JP2012/064253.
Third Party Observation, dated Feb. 12, 2013, in counterpart International Application No. PCT/JP2012/064253.
Anonymous, "Fluazinam Compositions," Research Disclosure, The Industry Standard Disclosure Publication Service, Mason Publications, Hampshire, GB, Oct. 2000, pp. 1-7.
Westerdijk, C. E. et al (ed), "PPO-Special Report No. 10," Applied Plant Research, Sep. 2004, pp. 1-8, 109-118.
Written Opinion, PCT/ISA/237, issued by the International Searching Authority in counterpart International Application No. PCT/JP2012/064253.
Communication dated May 6, 2015 issued by Egyptian Patent Office in counterpart Egyptian Patent Application No. 2013111795, received Jul. 5, 2015.

*Primary Examiner* — Raymond Henley, III
(74) *Attorney, Agent, or Firm* — Sughrue Mion, PLLC

(57) ABSTRACT

A composition having a stable and high fungicidal effect against a cultivated crop infected by a plant pathogen is provided. An agricultural or horticultural fungicide composition containing, as active ingredients, (a) fluazinam or its salt and (b) a strobilurin compound or its salt is provided; in addition, a method for controlling a plant pathogen by applying the subject agricultural or horticultural fungicide composition to a plant or a soil is provided; and furthermore, a method for controlling a plant pathogen by applying (a) fluazinam or its salt and (b) a strobilurin compound or its salt to a plant or a soil is provided.

5 Claims, No Drawings

AGRICULTURAL OR HORTICULTURAL FUNGICIDE COMPOSITION AND METHOD FOR CONTROLLING PLANT PATHOGEN

TECHNICAL FIELD

The present invention relates to an agricultural or horticultural fungicide composition in which a control effect against a plant pathogen, especially a preventive and/or therapeutic effect against a plant pathogen, is markedly enhanced; and a method for controlling a plant pathogen using the composition.

BACKGROUND ART

Patent Document 1 discloses that an N-pyridylaniline compound having a certain chemical structure is useful as an active ingredient for a harmful bio-organism controlling agent. In addition, this patent document also discloses that if desired, the N-pyridylaniline compound can be mixed with or used in combination with other pesticides, for example, an insecticide, a miticide, a fungicide, a plant growth regulator, etc.; and that in that case, a more excellent effect may be possibly exhibited. A fungicide, fluazinam, is included in the N-pyridylaniline compound.

Patent Document 2 discloses a fungicide composition containing azoxystrobin and fluazinam.

CITATION LIST

Patent Literature

Patent Literature 1: U.S. Pat. No. 4,331,670 A
Patent Literature 2: CN 101984817 A

SUMMARY OF INVENTION

Technical Problem

Since in a control effect against a plant pathogen, (a) fluazinam or its salt is insufficient in the effect against some of specific plant pathogens or is relatively short in residual efficacy, it does not practically exhibit a sufficient control effect against a plant pathogen in some conditions for application.

Solution to Problem

As a result of extensive and intensive investigations to solve the above-described problems, the present inventors have obtained such knowledge that use of (a) fluazinam or its salt in combination with (b) a strobilurin compound or its salt exhibits an unpredictable and excellent control effect against a plant pathogen as compared with the case of a single use of each compound and accomplished the present invention.

That is, the present invention relates to an agricultural or horticultural fungicide composition containing, as active ingredients, (a) fluazinam or its salt and (b) a strobilurin compound or its salt. In addition, the present invention relates to a method for controlling a plant pathogen by applying the above-described agricultural or horticultural fungicide composition to a plant or a soil. Furthermore, the present invention relates to a method for controlling a plant pathogen by applying the above-described (a) and (b) to a plant or a soil.

Advantageous Effects of Invention

The agricultural or horticultural fungicide composition of the present invention has a preventive and/or therapeutic effect and has a stable and high control effect against a cultivated crop infected by a plant pathogen, and the plant pathogen can be controlled by using this composition.

DESCRIPTION OF EMBODIMENTS

Fluazinam (common name) as the above-described (a) is 3-chloro-N-(3-chloro-5-trifluoromethyl-2-pyridyl)-α,α,α-trifluoro-2,6-dinitro-p-toluidine.

Examples of the strobilurin compound as the above-described (b) include azoxystrobin, kresoxim-methyl, pyraclostrobin, trifloxystrobin, dimoxystrobin, fluoxastrobin, metominostrobin, orysastrobin, picoxystrobin, enestroburin, coumoxystrobin, enoxastrobin, flufenoxystrobin, pyraoxystrobin, pyrametostrobin, fenaminostrobin, triclopyricarb, pyribencarb, famoxadone, and fenamidone.

The azoxystrobin is a compound disclosed on pages of 62-64 of The Pesticide Manual (Fifteenth Edition; BRITISH CROP PROTECTION COUNCIL).

The kresoxim-methyl is a compound disclosed on pages of 688-690 of The Pesticide Manual (Fifteenth Edition; BRITISH CROP PROTECTION COUNCIL).

The pyraclostrobin is a compound disclosed on pages of 971-972 of The Pesticide Manual (Fifteenth Edition; BRITISH CROP PROTECTION COUNCIL).

The trifloxystrobin is a compound disclosed on pages of 1167-1169 of The Pesticide Manual (Fifteenth Edition; BRITISH CROP PROTECTION COUNCIL).

The dimoxystrobin is a compound disclosed on pages of 383-384 of The Pesticide Manual (Fifteenth Edition; BRITISH CROP PROTECTION COUNCIL).

The fluoxastrobin is a compound disclosed on pages of 538-540 of The Pesticide Manual (Fifteenth Edition; BRITISH CROP PROTECTION COUNCIL).

The metominostrobin is a compound disclosed on pages of 783-784 of The Pesticide Manual (Fifteenth Edition; BRITISH CROP PROTECTION COUNCIL).

The orysastrobin is a compound disclosed on pages of 840-841 of The Pesticide Manual (Fifteenth Edition; BRITISH CROP PROTECTION COUNCIL).

The picoxystrobin is a compound disclosed on pages of 910-911 of The Pesticide Manual (Fifteenth Edition; BRITISH CROP PROTECTION COUNCIL).

The enestroburin is a compound disclosed in EP-A-936213.

The coumoxystrobin is a compound disclosed on page 4 of Fungicides Resistance Action Committee (FRAC) Code List 2012: Fungicides sorted by mode of action.

The enoxastrobin is a compound disclosed on page 4 of Fungicides Resistance Action Committee (FRAC) Code List 2012: Fungicides sorted by mode of action.

The flufenoxystrobin is a compound disclosed on page 4 of Fungicides Resistance Action Committee (FRAC) Code List 2012: Fungicides sorted by mode of action.

The pyraoxystrobin is a compound disclosed on page 4 of Fungicides Resistance Action Committee (FRAC) Code List 2012: Fungicides sorted by mode of action.

The pyrametostrobin is a compound disclosed on page 4 of Fungicides Resistance Action Committee (FRAC) Code List 2012: Fungicides sorted by mode of action.

The fenaminostrobin is a compound disclosed on page 4 of Fungicides Resistance Action Committee (FRAC) Code List 2012: Fungicides sorted by mode of action.

The triclopyricarb is a compound disclosed on page 4 of Fungicides Resistance Action Committee (FRAC) Code List 2012: Fungicides sorted by mode of action.

The pyribencarb is a compound disclosed on page 4 of Fungicides Resistance Action Committee (FRAC) Code List 2012: Fungicides sorted by mode of action.

The famoxadone is a compound disclosed on pages of 458-459 of The Pesticide Manual (Fifteenth Edition; BRITISH CROP PROTECTION COUNCIL).

The fenamidone is a compound disclosed on pages of 462-463 of The Pesticide Manual (Fifteenth Edition; BRITISH CROP PROTECTION COUNCIL).

As the salt which is included in the above-described (a) or (b) in the present invention, all of agriculturally acceptable salts may be used. Examples thereof include alkali metal salts such as sodium salts and potassium salts; alkaline earth metal salts such as magnesium salts and calcium salts; ammonium salts such as monoethylammonium salts, dimethylammonium salts, and triethylammonium salts; inorganic acid salts such as hydrochlorides, perchlorates, sulfates, and nitrates; and organic acid salts such as acetates and methanesulfonates.

A mixing ratio of the above-described (a) and (b) in the present invention may vary depending upon various conditions such as a kind of compound to be mixed, a subject crop, a use method, a formulation form, an application amount, an application time, and a kind of harmful pathogen and cannot be unequivocally defined. However, it is usually from 1:10, 000 to 10,000:1, preferably from 1:2,000 to 2,000:1, and more preferably from 1:1,000 to 1,000:1 in terms of a (a):(b) weight ratio.

In addition, in the case where the above-described (b) is metominostrobin, the (a):(b) weight ratio is preferably from 1:2,500 to 2, 500:1.

A method for controlling a plant pathogen by applying the agricultural or horticultural fungicide composition of the present invention to a plant or a soil is also included in the present invention. A use concentration of each of the active ingredients of the agricultural or horticultural fungicide composition of the present invention may vary depending upon various conditions such as a kind of compound to be mixed, a subject crop, a use method, a formulation form, an application amount, an application time, and a kind of harmful pathogen and cannot be unequivocally defined. However, the concentration of the active ingredient is usually from 0.01 to 1,000 ppm, preferably from 0.01 to 500 ppm, and more preferably from 0.01 to 200 ppm for (a); and usually from 0.1 to 10,000 ppm, preferably from 0.1 to 5,000 ppm, and more preferably from 0.1 to 200 ppm for (b), respectively.

The agricultural or horticultural fungicide composition comprising the above-described (a) and (b) as active ingredients exhibits an excellent fungicidal activity by applying cultivated crops, for example, vegetables such as cucumbers, tomatoes, and eggplants; cereals such as rice and wheat; peas; fruit trees such as apples, pears, grapes and citrus; and potatoes, which are infected or have a possibility to be infected by harmful pathogens, it is desirable for controlling diseases such as powdery mildew, downy mildew, anthracnose, gray mold, common green mold, scab, *alternaria* blotch, bacterial blight, black spot, black spot disease, ripe rot, late blight, ring spot, blast, sheath blight, seedling blight and southern blight. In addition, the agricultural or horticultural fungicide composition of the present invention exhibits an excellent control effect against soil-borne diseases caused by plant pathogens, such as *Fusarium, Rhizoctonia, Verticillium, Plasmodiophora*, and *Pythium*. The agricultural or horticultural fungicide composition of the present invention has a long residual efficacy and especially it is excellent in a preventive effect.

The agricultural or horticultural fungicide composition of the present invention exhibits a control effect against a disease, such as rice blast; rice sheath blight; cucumber anthracnose; downy mildew of cucumbers, melons, cabbages, Chinese cabbages, onions, pumpkins, and grapes; powdery mildew of wheat, barley, and cucumbers; blight of potatoes, red peppers, sweet peppers, watermelons, pumpkins, tobaccos, and tomatoes; wheat *Septoria* disease; tomato early blight; citrus melanose; citrus common green mold; pear scab; apple *alternaria* blotch; onion white tip; watermelon brown rot; various gray mold; various crown rot; various rust; various bacterial blight; and various soil-borne diseases caused by plant pathogenic fungi, such as *Fusarium, Pythium, Rhizoctonia*, and *Verticillium*. In addition, the agricultural or horticultural fungicide composition exhibits an excellent control effect against diseases caused by *Plasmodiophora*. More specifically, the composition exhibits an especially excellent control effect against diseases such as blight of potatoes, red peppers, sweet peppers, watermelons, pumpkins, tobaccos, and tomatoes; downy mildew of cucumbers, melons, cabbages, Chinese cabbages, onions, pumpkins, and grapes; and diseases of turf such as *Pythium* blight, *Pythium* red blight and *Rhizoctonia* rot (brown patch and large patch).

The active ingredients which constitute the agricultural or horticultural fungicide composition of the present invention can be formulated into a variety of forms, such as emulsifiable concentrates, dustable powders, wettable powders, soluble concentrates, granules, suspension concentrates, etc., together with various adjuvants, as in conventional agricultural preparations. The above-described (a) and other specific compounds may be mixed and formulated, or each of them may be separately formulated and then mixed together. Upon use, the preparation may be used as such or as diluted with an appropriate diluent, e.g., water, to a predetermined concentration. Examples of the adjuvants which can be used include carriers, emulsifying agents, suspending agents, thickeners, stabilizers, dispersants, spreaders, wetting agents, penetrating agents, antifreezing agents, antifoaming agents and the like. These adjuvants are added appropriately, if necessary. The carriers are classified into solid carriers and liquid carriers. The solid carriers include animal and vegetable powders (e.g., starch, sugar, cellulose powders, cyclodextrin, activated charcoal, soybean powders, wheat powders, chaff powders, wood powders, fish powders, powdery milk, etc.); mineral powders (e.g., talc, kaolin, bentonite, organic bentonite, calcium carbonate, calcium sulfate, sodium hydrogencarbonate, zeolite, diatomaceous earth, white carbon, clay, alumina, silica, sulfur powder, slaked lime, etc.); and the like. Examples of the liquid carriers include water, vegetable oils (e.g., soybean oil, cotton seed oil, etc.), animal oils (e.g., beef tallow, whale oil, etc.), alcohols (e.g., ethyl alcohol, ethylene glycol, etc.), ketones (e.g., acetone, methyl ethyl ketone, methyl isobutyl ketone, isophorone, etc.), ethers (e.g., dioxane, tetrahydrofuran, etc.), aliphatic hydrocarbons (e.g., kerosene, lamp oil, liquid paraffin, etc.), aromatic hydrocarbons (e.g., toluene, xylene, trimethylbenzene, tetramethylbenzene, cyclohexane, solvent naphtha, etc.), halogenated hydrocarbons (e.g., chloroform, chlorobenzene, etc.), acid amides (e.g., N-methyl-2-pyrrolidone, N,N-dimethylformamide, N,N-dimethylacetamide, etc.), esters (e.g., acetic acid ethyl ester, fatty acid glycerine esters, etc.), nitriles (e.g., acetonitrile, etc.), sulfur-containing compounds (e.g., dimethyl sulfoxide, etc.), and the like. Examples of the spreaders include sodium alkylsulfate, sodium alkylbenzene sulfonate, sodium lignin sulfonate, polyoxyethylene glycol alkyl ether, polyoxyethylene lauryl ether, polyoxyethylene alkyl aryl ether, polyoxyethylene sorbitan fatty acid ester and the like.

In addition, in the method of the present invention, the agricultural or horticultural fungicide composition of the present invention can be further mixed with other agricultural chemicals, such as a fungicide, an insecticide, a miticide, a nematicide, a soil insect pesticide, an antivirus agent, an attractant, a herbicide, a plant growth regulating agent and in this case, further excellent effect is exhibited in some cases. These compounds naturally include salt, alkyl ester, hydrate, different crystalline form, and various structural isomer and the like, when they exist, even where they are not especially described.

The active ingredient compounds of the fungicide in the above-mentioned other agricultural chemicals include, for example, (by common names, some of them are still in an application stage, or the test code of Japan Plant Protection Association):

anilinopyrimidinamine compounds, such as mepanipyrim, pyrimethanil, and cyprodinil;
triazolopyrimidine compounds such as 5-chloro-7-(4-methylpiperidin-1-yl)-6-(2,4,6-trifluorophenyl)[1,2,4]triazole[1,5-a]pyrimidine;
azole compounds, such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole, and imibenconazole;
quinoxaline compounds, such as quinomethionate;
dithiocarbamate compounds, such as maneb, zineb, mancozeb, polycarbamate, metiram, propineb, and thiram;
organic chlorine compounds, such as fthalide, chlorothalonil, quintozene;
imidazole compounds, such as benomyl, thiophanate-methyl, carbendazim, thiabendazole, fuberiazole, and cyazofamid;
cyanoacetamide compounds, such as cymoxanil;
anilide compounds, such as; metalaxyl, metalaxyl-M, mefenoxam, oxadixyl, ofurace, benalaxyl, benalaxyl-M (another name: kiralaxyl, chiralaxyl), furalaxyl, cyprofuram, carboxin, oxycarboxin, thifluzamide, boscalid, bixafen, isotianil, tiadinil, and sedaxane;
sulfenic acid compounds, such as dichlofluanid;
copper compounds, such as cupric hydroxide and oxine copper;
isoxazole compounds, such as hymexazol;
organophosphorus compounds such as fosetyl-aluminum (fosetyl-Al), tolclofos-methyl, S-benzyl O,O-diisopropylphosphorothioate, O-ethyl S,S-diphenylphosphorodithioate, aluminum ethylhydrogen phosphonate, edifenphos, and iprobenfos;
phthalimide compounds such as captan, captafol and folpet;
dicarboximide compounds, such as procymidone, iprodione, and vinclozolin;
benzanilide compounds, such as flutolanil and mepronil;
amide compounds, such as penthiopyrad, penflufen, furametpyr, isopyrazam, fenfuram, fluxapyroxad, silthiopham, and fenoxanil;
benzamide compounds, such as fluopyram and zoxamide;
piperazine compounds, such as triforine;
pyridine compounds, such as pyrifenox;
carbinol compounds, such as fenarimol;
piperidine compounds, such as fenpropidin;
morpholine compounds, such as fenpropimorph and tridemorph;
organotin compounds, such as fentin hydroxide and fentin acetate;
urea compounds, such as pencycuron;
cinnamic acid compounds, such as dimethomorph and flumorph;
phenylcarbamate compounds, such as diethofencarb;
cyanopyrrole compounds, such as fludioxonil and fenpiclonil;
thiazolecarboxamide compounds, such as ethaboxam;
valinamide compounds, such as iprovalicarb and benthiavalicarb-isopropyl;
acylaminoacid compounds, such as methyl N-(isopropoxycarbonyl)-L-valyl-(3RS)-3-(4-chlorophenyl)-β-alaninate (valiphenalate);
hydroxyanilide compounds, such as fenhexamid;
benzenesulfonamide compounds, such as flusulfamide;
oxime ether compounds, such as cyflufenamid;
anthraquinone compounds;
crotonic acid compounds;
antibiotics, such as validamycin, kasugamycin, and polyoxins;
guanidine compounds, such as iminoctadine and dodine;
quinoline compounds, such as tebufloquin;
thiazolidine compounds, such as flutianil;
and other compounds, such as isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, mandipropamid, fluopicolide, carpropamid, meptyldinocap, pyriofenone, N-[(3',4'-dichloro-1,1-dimethyl)phenacyl]-3-trifluoromethyl-2-pyridinecarboxamide, N-[(3',4'-dichloro-1,1-dimethyl)phenacyl]-3-methyl-2-thiophenecarboxamide, N-[(3',4'-dichloro-1,1-dimethyl)phenacyl]-1-methyl-3-trifluoromethyl-4-pyrazolecarboxamide, N-[[2'-methyl-4'-(2-propyloxy)-1,1-dimethyl]phenacyl]-3-trifluoromethyl-2-pyridinecarboxamide, N-[[2'-methyl-4'-(2-propyloxy)-1,1-dimethyl]phenacyl]-3-methyl-2-thiophenecarboxamide, N-[[2'-methyl-4'-(2-propyloxy)-1,1-dimethyl]phenacyl]-1-methyl-3-trifluoromethyl-4-pyrazolecarboxamide, N-[[4'-(2-propyloxy)-1,1-dimethyl]phenacyl]-3-trifluoromethyl-2-pyridinecarboxamide, N-[[4'-(2-propyloxy)-1,1-dimethyl]phenacyl]-3-methyl-2-thiophenecarboxamide, N-[[4'-(2-propyloxy)-1,1-dimethyl]phenacyl]-1-methyl-3-trifluoromethyl-4-pyrazolecarboxamide, N-[[2'-methyl-4'-(2-pentyloxy)-1,1-dimethyl]phenacyl]-3-trifluoromethyl-2-pyridinecarboxamide, N-[[4'-(2-pentyloxy)-1,1-dimethyl]phenacyl]-3-trifluoromethyl-2-pyridinecarboxamide, ferimzone, spiroxamine, fenpyrazamine, ametoctradin, S-2200, ZF-9646, BCF-051, BCM-061, BCM-062.

The active ingredient compounds of an insect pest control agents, such as the insecticide, the miticide, the nematicide, or the soil insecticide in the above-mentioned other agricultural chemicals, include, for example, (by common names, some of them are still in an application stage; or the test code of Japan Plant Protection Association):

organic phosphate ester compounds, such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet and phorate;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives, such as cartap, thiocyclam, bensultap, and thiosultap-sodium;

organic chlorine compounds, such as dicofol, tetradifon, endosulfan, dienochlor and dieldrin;

organic metal compounds, such as fenbutatin oxide and cyhexatin;

pyrethroid compounds, such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, and flumethrin;

benzoylurea compounds, such as diflubenzuron, chlorfluazuron, teflubenzuron, flufenoxuron, triflumuron, hexaflumuron, lufenuron, novaluron, noviflumuron, bistrifluoron, and fluazuron;

juvenile hormone-like compounds, such as methoprene, pyriproxyfen, fenoxycarb and diofenolan;

pyridazinone compounds, such as pyridaben;

pyrazole compounds, such as fenpyroximate, fipronil, tebufenpyrad, ethiprole, tolfenpyrad, acetoprole, pyrafluprole and pyriprole;

neonicotinoids, such as imidacloprid, nitenpyram, acetamiprid, thiacloprid, thiamethoxam, clothianidin, nidinotefuran, dinotefuran, and nithiazine;

hydrazine compounds, such as tebufenozide, methoxyfenozide, chromafenozide and halofenozide;

pyridine compounds, such as flonicamid;

tetronic acid compounds, such as spirodiclofen;

strobilurin compounds, such as fluacrypyrim;

pyridinamine compounds, such as flufenerim;

dinitro compounds; organic sulfur compounds; urea compounds; triazine compounds; hydrazone compounds;

other compounds, such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazone, fenazaquin, amidoflumet, chlorobenzoate, sulfluramid, hydramethylnon, metaldehyde, HGW-86, AKD-1022, ryanodine, pyridalyl, verbutin; and the like.

Further, it may be used in combination with or together with microbial pesticide, such as crystal protein toxin produced by *Bacillus thuringiensis* aizawai, *Bacillus thuringiensis* kurstaki, *Bacillus thuringiensis* israelenses, *Bacillus thuringiensis* japonensis, *Bacillus thuringiensis* tenebrionis, or *Bacillus thuringiensis*, entomopathogenic virus, entomopathogenic fungi, and nematophagous fungi;

antibiotics and spinetoram such as avermectin, emamectin benzoate, milbemectin, milbemycin, spinosad, ivermectin, lepimectin, DE-175, abamectin, emamectin and spinetoram;

natural products, such as azadirachtin and rotenone;

repellents, such as deet; and the like.

Next, some preferred embodiments of the agricultural or horticultural fungicide composition of the present invention are exemplified, but it should not be construed that the present invention is limited to these embodiments.

(1) An agricultural or horticultural fungicide composition comprising, as active ingredients, (a) fluazinam or its salt and (b) a strobilurin compound or its salt.

(2) The agricultural or horticultural fungicide composition described in the above (1), wherein the strobilurin compound (b) is at least one member selected from the group consisting of kresoxim-methyl, pyraclostrobin, trifloxystrobin, dimoxystrobin, fluoxastrobin, metominostrobin, orysastrobin, picoxystrobin, coumoxystrobin, enoxastrobin, flufenoxystrobin, pyraoxystrobin, fenaminostrobin, triclopyricarb, pyribencarb, famoxadone, and fenamidone.

(3) The agricultural or horticultural fungicide composition described in the above (1), wherein the strobilurin compound (b) is kresoxim-methyl, pyraclostrobin, trifloxystrobin, dimoxystrobin, metominostrobin, or picoxystrobin.

(4) The agricultural or horticultural fungicide composition described in the above (1), wherein the strobilurin compound (b) is kresoxim-methyl.

(5) The agricultural or horticultural fungicide composition described in the above (1), wherein the strobilurin compound (b) is pyraclostrobin.

(6) The agricultural or horticultural fungicide composition described in the above (1), wherein the strobilurin compound (b) is trifloxystrobin.

(7) The agricultural or horticultural fungicide composition described in the above (1), wherein the strobilurin compound (b) is dimoxystrobin.

(8) The agricultural or horticultural fungicide composition described in the above (1), wherein the strobilurin compound (b) is metominostrobin.

(9) The agricultural or horticultural fungicide composition described in the above (1), wherein the strobilurin compound (b) is picoxystrobin.

(10) A method for controlling a plant pathogen comprising applying an agricultural or horticultural fungicide composition containing, as active ingredients, (a) fluazinam or its salt and (b) a strobilurin compound or its salt to a plant or a soil.

(11) A method for controlling a plant pathogen comprising applying (a) fluazinam or its salt and (b) a strobilurin compound or its salt to a plant or a soil.

EXAMPLES

Next, Test Examples according to the present invention are described below, but it should not be construed that the present invention is limited to these Examples.

Test Example 1

Inhibition Test of Mycelial Growth Against the Genus Pythium (Pythium graminicola)

A mycangium (diameter: 4 mm) obtained by precultivation was transplanted on PSA containing a chemical in a prescribed concentration and then cultured at room temperature of 20° C. for 3 days, followed by measuring a diameter of the grown mycangium to determine an inhibition rate of mycelial growth (%).

Results are shown in Tables 1 to 3.

In addition, an expected value of the inhibition rate was calculated according to the following Colby's formula and listed in parentheses of Tables 1 to 3. In the case where an experimental value is higher than an expected value according to the Colby's formula, the agricultural or horticultural fungicide composition of the present invention exhibits a synergistic effect on controlling of a plant pathogen. Colby's formula: $x+y-xy/100$ x: Inhibition rate of growth of the component (a) alone (%)
y: Inhibition rate of growth of the component (b) alone (%)

TABLE 1

Inhibition Rate of Mycelial Growth against *Pythium graminicola* (%) (expected value)

| azoxystrobin | fluazinam | | | | |
| --- | --- | --- | --- | --- | --- |
| | 100 ppm | 10 ppm | 1 ppm | 0.1 ppm | 0 ppm |
| 100 ppm | 100 (100) | 100 (100) | 100 (100) | 100 (100) | 100 |
| 10 ppm | 100 (96.3) | 100 (95.6) | 100 (94.3) | 100 (92.5) | 89 |
| 0 ppm | 66 | 60 | 48 | 32 | |

TABLE 2

Inhibition Rate of Mycelial Growth against *Pythium graminicola* (%) (expected value)

| kresoxim-methyl | fluazinam | | | |
| --- | --- | --- | --- | --- |
| | 100 ppm | 10 ppm | 1 ppm | 0 ppm |
| 100 ppm | 96 (87.1) | 92 (84.8) | 89 (80.2) | 62 |
| 10 ppm | 92 (90.8) | 98 (89.2) | 94 (86.0) | 73 |
| 1 ppm | 88 (85.0) | 86 (82.4) | 84 (77.1) | 56 |
| 0 ppm | 66 | 60 | 48 | |

TABLE 3

Inhibition Rate of Mycelial Growth against *Pythium graminicola* (%) (expected value)

| pyraclostrobin | fluazinam | | | | |
| --- | --- | --- | --- | --- | --- |
| | 100 ppm | 10 ppm | 1 ppm | 0.1 ppm | 0 ppm |
| 100 ppm | 100 (100) | 100 (100) | 100 (100) | 100 (100) | 100 |
| 10 ppm | 100 (100) | 100 (100) | 100 (100) | 100 (100) | 100 |
| 1 ppm | 100 (94.2) | 100 (93.2) | 99 (91.2) | 93 (88.4) | 83 |
| 0 ppm | 66 | 60 | 48 | 32 | |

Test Example 2

Inhibition Test of Mycelial Growth Against the Genus Rhizoctonia (Rhizoctonia solani)

A mycangium (diameter: 4 mm) obtained by precultivation was transplanted on PSA containing a chemical in a prescribed concentration and then cultured at room temperature of 20° C. for 4 days, followed by measuring a diameter of the grown mycangium to determine an inhibition rate of mycelial growth (%).

Results are shown in Tables 4 to 6.

In addition, an expected value of the inhibition rate calculated according to the Colby's formula in the same manner as that in the foregoing Test Example 1 was listed in parentheses of Tables 4 to 6.

TABLE 4

Inhibition Rate of Mycelial Growth against *Rhizoctonia solani* (%) (expected value)

| azoxystrobin | fluazinam | | | | |
| --- | --- | --- | --- | --- | --- |
| | 100 ppm | 10 ppm | 1 ppm | 0.1 ppm | 0 ppm |
| 10 ppm | 100 (92.3) | 100 (91.2) | 100 (86.4) | 96 (82.3) | 41 |
| 1 ppm | 99 (91.8) | 90 (89.1) | 92 (83.2) | 85 (78.1) | 27 |
| 0.1 ppm | 92 (87.5) | 100 (85.6) | 90 (77.9) | 84 (71) | 4 |
| 0 ppm | 87 | 85 | 77 | 70 | |

TABLE 5

Inhibition Rate of Mycelial Growth against *Rhizoctonia solani* (%) (expected value)

| kresoxim-methyl | fluazinam | | | | |
| --- | --- | --- | --- | --- | --- |
| | 100 ppm | 10 ppm | 1 ppm | 0.1 ppm | 0 ppm |
| 10 ppm | 100 (92.5) | 100 (91.3) | 100 (86.7) | 91 (82.6) | 42 |
| 1 ppm | 100 (92.1) | 100 (90.9) | 93 (86.0) | 86 (81.7) | 39 |
| 0.1 ppm | 100 (90.9) | 97 (89.5) | 84 (83.9) | 85 (79.0) | 30 |
| 0 ppm | 87 | 85 | 77 | 70 | |

TABLE 6

Inhibition Rate of Mycelial Growth against *Rhizoctonia solani* (%) (expected value)

| pyraclostrobin | fluazinam | | | | |
| --- | --- | --- | --- | --- | --- |
| | 100 ppm | 10 ppm | 1 ppm | 0.1 ppm | 0 ppm |
| 10 ppm | 100 (95.7) | 100 (95.1) | 100 (92.4) | 100 (90.1) | 67 |
| 1 ppm | 93 (94.2) | 96 (93.3) | 97 (89.7) | 87 (86.5) | 55 |
| 0.1 ppm | 92 (90.4) | 99 (88.9) | 89 (83.0) | 79 (77.8) | 26 |
| 0 ppm | 87 | 85 | 77 | 70 | |

Test Example 3

Inhibition Test of Mycelial Growth Against Gray Mold (Botrytis cinerea)

On a YS (yeast extract+sucrose) liquid culture medium, a certain amount of a chemical solution prepared such that a final concentration of each chemical became a concentration at which the test was carried out was mixed. 100 μL of each of the chemical-containing YS liquid culture media was aliquoted into each well of a 96-well microplate. Thereafter, 50 μL of a spore suspension of gray mold whose spore concentration had been prepared as shown in the following tables was aliquoted into each well and cultivated at 25° C. under a light-dark cycle (light period: 16 hours, dark period: 8 hours). Three days after the cultivation, an area of the well bottom covered by the propagated gray mold hyphae was microscopically examined to determine an inhibition rate of growth (%). The inhibition rate of growth was visually examined while defining an area covered by hyphae in a non-treated well as 100. For the non-treatment, a chemical-free YS liquid culture medium was used.

In addition, an expected value of the inhibition rate calculated according to the Colby's formula in the same manner as that in the foregoing Test Example 1 was listed in parentheses of Tables 7 to 13.

TABLE 7

Inhibition Rate of Mycelial Growth against *Botrytis cinerea* (%) (expected value)

| azoxystrobin | fluazinam | | | |
|---|---|---|---|---|
| | 0.16 ppm | 0.08 ppm | 0.04 ppm | 0 ppm |
| 12.5 ppm | 99 (80.2) | 90 (1) | 60 (1) | 1 |
| 6.25 ppm | 95 (80) | 85 (0) | 30 (0) | 0 |
| 3.13 ppm | 95 (80) | 65 (0) | 15 (0) | 0 |
| 0 ppm | 80 | 0 | 0 | — |

TABLE 8

Inhibition Rate of Mycelial Growth against *Botrytis cinerea* (%) (expected value)

| kresoxim-methyl | fluazinam | | | |
|---|---|---|---|---|
| | 0.16 ppm | 0.08 ppm | 0.04 ppm | 0 ppm |
| 12.5 ppm | 100 (80.2) | 95 (1) | 85 (1) | 1 |
| 6.25 ppm | 100 (80.2) | 95 (1) | 75 (1) | 1 |
| 3.13 ppm | 100 (80) | 97 (0) | 65 (0) | 0 |
| 0 ppm | 80 | 0 | 0 | — |

TABLE 9

Inhibition Rate of Mycelial Growth against *Botrytis cinerea* (%) (expected value)

| pyraclostrobin | fluazinam | | | |
|---|---|---|---|---|
| | 0.16 ppm | 0.08 ppm | 0.04 ppm | 0 ppm |
| 1.56 ppm | 99 (81) | 95 (5) | 90 (5) | 5 |
| 0.78 ppm | 98 (80.2) | 90 (1) | 85 (1) | 1 |
| 0.39 ppm | 95 (80) | 85 (0) | 45 (0) | 0 |
| 0 ppm | 80 | 0 | 0 | — |

TABLE 10

Inhibition Rate of Mycelial Growth against *Botrytis cinerea* (%) (expected value)

| trifloxystrobin | fluazinam | | | |
|---|---|---|---|---|
| | 0.16 ppm | 0.08 ppm | 0.04 ppm | 0 ppm |
| 1.56 ppm | 100 (80) | 90 (0) | 65 (0) | 0 |
| 0.78 ppm | 99 (80) | 85 (0) | 55 (0) | 0 |
| 0.39 ppm | 95 (80) | 85 (0) | 45 (0) | 0 |
| 0 ppm | 80 | 0 | 0 | — |

TABLE 11

Inhibition Rate of Mycelial Growth against *Botrytis cinerea* (%) (expected value)

| picoxystrobin | fluazinam | | | |
|---|---|---|---|---|
| | 0.16 ppm | 0.08 ppm | 0.04 ppm | 0 ppm |
| 25 ppm | 98 (80.6) | 90 (3) | 85 (3) | 3 |
| 12.5 ppm | 99 (80.4) | 98 (2) | 85 (2) | 2 |
| 6.25 ppm | 100 (80.2) | 95 (1) | 70 (1) | 1 |
| 0 ppm | 80 | 0 | 0 | — |

TABLE 12

Inhibition Rate of Mycelial Growth against *Botrytis cinerea* (%) (expected value)

| dimoxystrobin | fluazinam | | | |
|---|---|---|---|---|
| | 0.16 ppm | 0.08 ppm | 0.04 ppm | 0 ppm |
| 3.13 ppm | 100 (80) | 95 (0) | 60 (0) | 0 |
| 1.56 ppm | 98 (80) | 85 (0) | 40 (0) | 0 |
| 0.78 ppm | 100 (80) | 80 (0) | 40 (0) | 0 |
| 0 ppm | 80 | 0 | 0 | — |

TABLE 13

Inhibition Rate of Mycelial Growth against *Botrytis cinerea* (%) (expected value)

| metominostrobin | fluazinam | | | |
|---|---|---|---|---|
| | 0.16 ppm | 0.08 ppm | 0.04 ppm | 0 ppm |
| 100 ppm | 100 (80.6) | 97 (3) | 85 (3) | 3 |
| 50 ppm | 99 (80.2) | 95 (1) | 65 (1) | 1 |
| 25 ppm | 99 (80) | 95 (0) | 15 (0) | 0 |
| 0 ppm | 80 | 0 | 0 | — |

While the invention has been described in detail and with reference to specific embodiments thereof, it will be apparent to one skill in the art that various changes and modifications can be made therein without departing from the sprit and scope thereof.

This application is based on Japanese patent application No. 2011-117097 filed on May 25, 2011, the entire contents of which are incorporated hereinto by reference. All references cited herein are incorporated in their entirety.

INDUSTRIAL APPLICABILITY

The agricultural or horticultural fungicide composition of the present invention has a preventive and/or therapeutic effect and has a stable and high control effect against a cultivated crop infected by a plant pathogen, and the plant pathogen can be controlled by using this composition.

The invention claimed is:

1. An agricultural or horticultural fungicide composition comprising, as active ingredients, (a) fluazinam or a salt thereof and (b) a strobilurin compound or a salt thereof.

2. The agricultural or horticultural fungicide composition according to claim 1, wherein the strobilurin compound (b) is at least one member selected from the group consisting of kresoxim-methyl, pyraclostrobin, trifloxystrobin, dimoxystrobin, fluoxastrobin, metominostrobin, orysastrobin, picoxystrobin, coumoxystrobin, enoxastrobin, flufenoxystrobin, pyraoxystrobin, fenaminostrobin, triclopyricarb, pyribencarb, famoxadone, and fenamidone.

3. The agricultural or horticultural fungicide composition according to claim 1, wherein the strobilurin compound (b) is at least one member selected from the group consisting of kresoxim-methyl, pyraclostrobin, trifloxystrobin, dimoxystrobin, metominostrobin, and picoxystrobin.

4. A method for controlling a plant pathogen comprising applying an agricultural or horticultural fungicide composition containing, as active ingredients, (a) fluazinam or a salt thereof and (b) a strobilurin compound or a salt thereof to a plant or a soil.

5. A method for controlling a plant pathogen comprising applying (a) fluazinam or a salt thereof and (b) a strobilurin compound or a salt thereof to a plant or a soil.

* * * * *